US008481765B2

(12) United States Patent
Hofen et al.

(10) Patent No.: US 8,481,765 B2
(45) Date of Patent: Jul. 9, 2013

(54) METHOD FOR THE PRODUCTION OF EPICHLOROHYDRIN

(75) Inventors: Willi Hofen, Rodenbach (DE); Claudia Brasse, Hanau (DE); Robert Franke, Marl (DE); Robert Katzer, Frankfurt am Main (DE)

(73) Assignee: Momentive Specialty Chemicals Inc., Columbus, OH (US)

( * ) Notice: Subject to any disclaimer, the term of this patent is extended or adjusted under 35 U.S.C. 154(b) by 273 days.

(21) Appl. No.: 12/919,637

(22) PCT Filed: Dec. 16, 2008

(86) PCT No.: PCT/EP2008/067584
§ 371 (c)(1),
(2), (4) Date: Nov. 15, 2010

(87) PCT Pub. No.: WO2009/115152
PCT Pub. Date: Sep. 24, 2009

(65) Prior Publication Data
US 2011/0054197 A1 Mar. 3, 2011

(30) Foreign Application Priority Data

Mar. 17, 2008 (EP) .................... 08102653

(51) Int. Cl.
*C07D 301/12* (2006.01)
*C07D 301/06* (2006.01)
(52) U.S. Cl.
USPC .......................... 549/533; 549/531
(58) Field of Classification Search
USPC .................. 549/531, 533
See application file for complete search history.

(56) References Cited

U.S. PATENT DOCUMENTS

| 4,824,976 A | 4/1989 | Clerici et al. |
| 4,937,216 A | 6/1990 | Clerici et al. |
| 5,284,944 A | 2/1994 | Madison et al. |
| 5,466,836 A | 11/1995 | Jubin, Jr. |
| 5,681,789 A | 10/1997 | Saxton et al. |
| 5,840,934 A | 11/1998 | Goto et al. |
| 5,973,171 A | 10/1999 | Cochran et al. |
| 6,037,484 A | 3/2000 | Grey |

(Continued)

FOREIGN PATENT DOCUMENTS
CN 1456582 A1 11/2003
CN 100516056 C 7/2009

(Continued)

OTHER PUBLICATIONS

P.L. Alsters et al., "Fine-Tuning and Recycling of Homogeneous Tungstate and Polylungstate Expoxidation Catalysts", Mechanisms in Homogeneous and Heterogeneous Epoxidation Catalysis (2008) 415-428, Elsivier B.V. and Technology.

(Continued)

*Primary Examiner* — Taylor Victor Oh

(57) ABSTRACT

The invention relates to a method for the production of epichlorohydrin, wherein a chloropropane-containing ally chloride in excess is reacted in a first reaction stage with hydrogen peroxide. The non-reacted ally chloride is separated and returned to the reaction, wherein part of the separated ally chloride is added to a second reaction stage and reacted with hydrogen peroxide, wherein the hydrogen peroxide quantity is selected in the second reaction stage such that the ally chloride is largely reacted. The chloropropanes are separated from the reaction mixture of the second reaction stage by means of distillation and removed from the process.

9 Claims, 1 Drawing Sheet

U.S. PATENT DOCUMENTS

| | | | |
|---|---|---|---|
| 6,054,407 | A | 4/2000 | Schulz et al. |
| 6,187,935 | B1 | 2/2001 | Gosselin et al. |
| 6,288,248 | B1 | 9/2001 | Strebelle |
| 6,300,506 | B1 | 10/2001 | Paparatto et al. |
| 6,350,888 | B1 | 2/2002 | Strebelle et al. |
| 6,380,407 | B1 | 4/2002 | Catinat et al. |
| 6,500,969 | B1 | 12/2002 | Zhou et al. |
| 6,541,648 | B1 | 4/2003 | Paparatto et al. |
| 6,590,112 | B1 | 7/2003 | Catinat et al. |
| 6,596,881 | B2 | 7/2003 | Haas et al. |
| 6,596,883 | B2 | 7/2003 | Hofen et al. |
| 6,624,318 | B1 | 9/2003 | MUller et al. |
| 6,673,950 | B1 | 1/2004 | Teles et al. |
| 6,815,552 | B2 | 11/2004 | Strebelle et al. |
| 7,141,683 | B2 | 11/2006 | Haas et al. |
| 7,205,419 | B2 | 4/2007 | Strebelle et al. |
| 7,320,779 | B2 | 1/2008 | Strebelle et al. |
| 7,323,578 | B2 | 1/2008 | Catinat et al. |
| 7,541,479 | B1 | 6/2009 | Chang et al. |
| 7,722,847 | B2 | 5/2010 | Haas et al. |
| 2001/0012909 | A1 | 8/2001 | Mizuno |
| 2003/0035771 | A1 | 2/2003 | Hasenzahl |
| 2003/0055293 | A1 | 3/2003 | Wurziger et al. |
| 2003/0078160 | A1 | 4/2003 | Hasenzahl et al. |
| 2003/0103894 | A1 | 6/2003 | Hasenzahl et al. |
| 2003/0109726 | A1 | 6/2003 | Balthasart |
| 2003/0144535 | A1 | 7/2003 | Teles et al. |
| 2003/0158431 | A1 | 8/2003 | Balthasart et al. |
| 2003/0187285 | A1 | 10/2003 | Balthsart |
| 2004/0039216 | A1 | 2/2004 | Balthasart |
| 2004/0054200 | A1 | 3/2004 | Paparatto et al. |
| 2004/0068128 | A1 | 4/2004 | Teles et al. |
| 2004/0142843 | A1 | 7/2004 | Schlingloff et al. |
| 2004/0151658 | A1 | 8/2004 | Escrig et al. |
| 2004/0181081 | A1 | 9/2004 | Forlin et al. |
| 2005/0222440 | A1 | 10/2005 | Khan et al. |
| 2005/0250955 | A1 | 11/2005 | Goebbel et al. |
| 2006/0025637 | A1 | 2/2006 | Babler et al. |
| 2006/0041150 | A1 | 2/2006 | Catinat et al. |
| 2006/0167288 | A1 | 7/2006 | Strebelle et al. |
| 2006/0216216 | A1 | 9/2006 | Bassler et al. |
| 2006/0264633 | A1 | 11/2006 | Schlingloff et al. |
| 2007/0142651 | A1 | 6/2007 | Le-Khac et al. |
| 2010/0056814 | A1 | 3/2010 | Chang et al. |
| 2010/0094031 | A1 | 4/2010 | Trent et al. |
| 2010/0168379 | A1 | 7/2010 | Krafft et al. |
| 2010/0179300 | A1 | 7/2010 | Boulos et al. |
| 2010/0197947 | A1 | 8/2010 | Narahara et al. |
| 2010/0204494 | A1 | 8/2010 | Hatano |
| 2010/0331557 | A1 | 12/2010 | Strebelle et al. |

FOREIGN PATENT DOCUMENTS

| | | | |
|---|---|---|---|
| CN | 201713456 | U | 1/2011 |
| CN | 101993423 | A | 3/2011 |
| CN | 101293882 | B | 4/2011 |
| EP | 0936219 | A1 | 8/1999 |
| JP | 2005-154340 | | 6/2005 |
| WO | WO 99/23052 | | 5/1999 |
| WO | WO 00/76989 | | 12/2000 |
| WO | WO 01/64581 | | 9/2001 |
| WO | WO 01/64582 | | 9/2001 |
| WO | WO 01/72419 | | 10/2001 |
| WO | WO 02/00634 | | 1/2002 |
| WO | WO 02/14298 | | 2/2002 |
| WO | WO 03/18567 | | 3/2003 |
| WO | WO 2004/028962 | | 4/2004 |
| WO | WO 2004/029032 | | 4/2004 |
| WO | WO 2004/043941 | | 5/2004 |
| WO | WO 2004/048353 | | 6/2004 |
| WO | WO 2004/074268 | | 9/2004 |
| WO | WO 2005/095370 | A1 | 10/2005 |
| WO | WO 2006/108784 | | 10/2006 |
| WO | WO 2008/098921 | | 2/2007 |
| WO | WO 2008/057657 | A2 | 7/2008 |
| WO | WO 2008/078861 | A1 | 7/2008 |
| WO | WO 2009/063487 | A2 | 5/2009 |
| WO | WO 2009/129355 | | 10/2009 |
| WO | WO 2010/010003 | | 1/2010 |
| WO | WO 2011/032666 | | 3/2011 |

OTHER PUBLICATIONS

I.W.C.E. Arends et al., "Recent Developments in Selective catalystic expoxidations with H2O2", Topics in Catalysts, vol. 19, No. 1(2002) 133-141.

F.C. Frostick Jr., "Synthesis of Some Epoxy Vinyl Monomers by Epoxidation with Peracetic Acid", by J. Am. Chem. Soc. 81 (1958) 3350-3356.

N. Hoffman et al., "Liquid-Liquid Biphasic, Platinum-Catalyzed Hydrosilylation of Allyl Chloride with Trichlorosilane Using an Ionic Liquid Catalyst Phase in a Continuous Loop Reactor", Adv. Synth. Catal. (2008) 350, 2599-2609.

R. MBeleck et al. "Stability and recycling of polymer-supported Mo(VI) alkene epoxidation catalysts", Reactive & Functional Polymers 67 (2007) 1448-1457, Elsevier Sciences Publishers BV, Netherlands.

L. Ningning et al., "Epoxidation of Various Functionalized Olefins by a Ti-MWW/H2O2 Catalytic System", Chin J Catal (2008) vol. 29 Issue 2, 102-104.

P. Wu et al., "A novel titanosilicate with MWW structure Catalytic properties in selective epoxidation of diallyl ether with hydrogen peroxide" Journal of Catalysis 228 (2004) 183-191.

Wang, Lingling, et al., "Highly Efficient Synthesis of Epichlorohydrin by epoxidation of Allyl chloride over titanosillcate Ti-MWW", Chinese Journal of Catalysts (2006) vol. 27 Issue 8, 656-658.

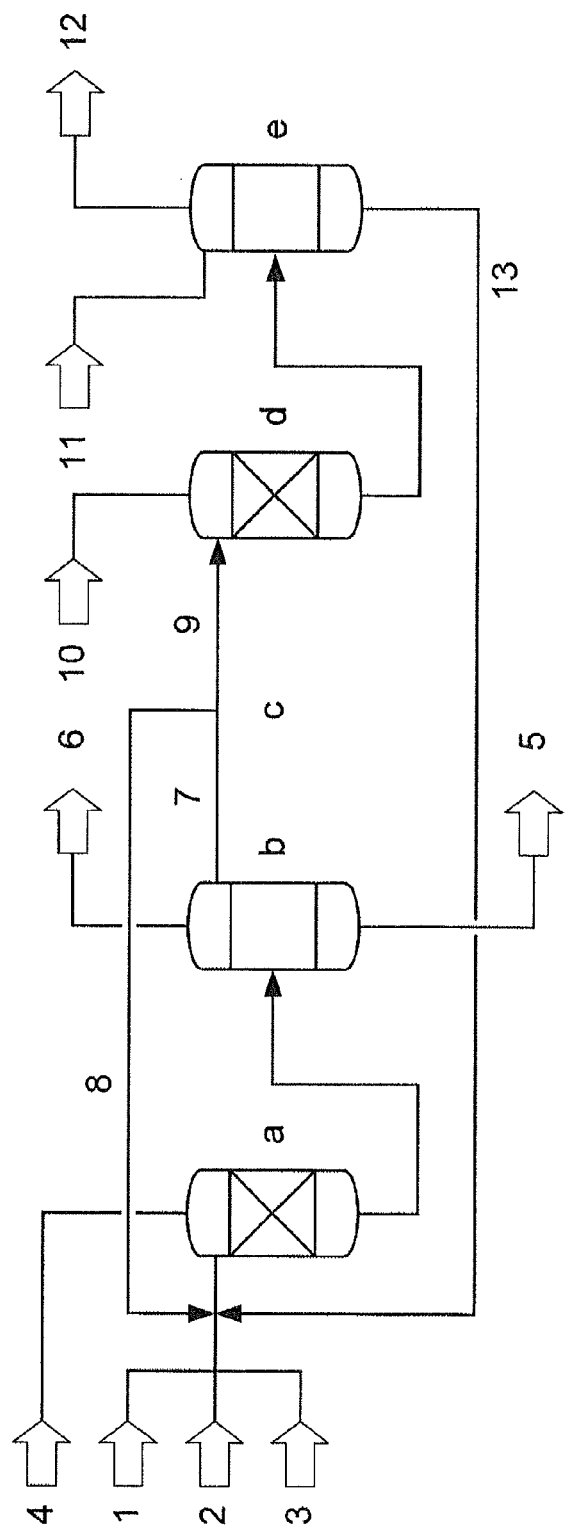

METHOD FOR THE PRODUCTION OF EPICHLOROHYDRIN

RELATED APPLICATION DATA

This application claims the benefit of PCT Application PCT/EP2008/067584 with International Filing Date of Dec. 16, 2008, published as WO 2009/115152 A1, which further claims priority to European Patent Application No. 20080102653 filed Mar. 17, 2008, the entire contents of both are hereby incorporated by reference.

DETAILED DESCRIPTION

The invention relates to a process for the preparation of epichlorohydrin by reacting allyl chloride with hydrogen peroxide.

Epichlorohydrin (chloromethyloxirane) is an important chemical intermediate which is used, for example, for the manufacture of resins.

A process suitable for the preparation of epichlorohydrin is the reaction, known from EP-A 0 100 119, of allyl chloride with hydrogen peroxide in the presence of a titanium-containing zeolite catalyst. In order to obtain a high selectivity for epichlorohydrin in this reaction, allyl chloride has to be used in a stoichiometric excess relative to hydrogen peroxide, as is known, for example, from WO 2004/043941. Unreacted allyl chloride can be separated off by distillation and be returned to the epoxidation reaction, as is known, for example, from WO 02/00634 or WO 02/14298.

Technical-grade allyl chloride is generally contaminated with 1-chloropropane and/or 2-chloropropane. Both impurities have similar boiling points to allyl chloride:
allyl chloride: 45° C.
1-chloropropane: 47° C.
2-chloropropane: 36° C.

The two chloropropanes can therefore only be separated off from allyl chloride by distillation with great complexity. Using a technical-grade allyl chloride contaminated with chloropropanes for the reaction of allyl chloride with hydrogen peroxide, and separating off unreacted allyl chloride by distillation and returning it to the epoxidation reaction accordingly result in an enrichment of chloropropanes in the process.

It is known from WO 02/00634 and WO 02/14298 that an enrichment of impurities in the recycled, unreacted olefin to undesirably high concentrations can be prevented by removing some of the recycled olefin from the process. The removed substream, however, comprises a high fraction of olefin which is lost as a result of the removal.

There is therefore a need for a process for the preparation of epichlorohydrin by reacting an allyl chloride containing chloropropanes with a high selectivity for epichlorohydrin and an improved conversion of the allyl chloride used compared with the known processes.

This object is achieved by a process according to the invention in which, in a first reaction stage, an allyl chloride containing chloropropanes is reacted in excess with hydrogen peroxide. The unreacted allyl chloride is separated off and returned to the reaction, where some of the separated-off allyl chloride is passed to a second reaction stage and reacted with hydrogen peroxide, where the amount of hydrogen peroxide in the second reaction stage is chosen such that the allyl chloride is reacted largely and preferably virtually completely. The chloropropanes can then be separated off from the reaction mixture of the second reaction stage by distillation without losses of allyl chloride. Since in the process according to the invention the majority of the allyl chloride is reacted in an excess of allyl chloride and only a small part of the allyl chloride reacts in a low excess or a substoichiometric amount of allyl chloride, the high selectivity for epichlorohydrin effected by an excess of allyl chloride is retained.

The invention therefore provides a process for the preparation of epichlorohydrin in which a) in a first reaction stage, allyl chloride and hydrogen peroxide are reacted in the presence of a titanium-containing zeolite catalyst in a molar ratio of allyl chloride to hydrogen peroxide of at least 1.5:1 and where the allyl chloride used is 1-chloropropane and/or 2-chloropropane, b) the reaction mixture formed in the first reaction stage is separated in a distillation into a mixture (A) which comprises unreacted allyl chloride, and also 1-chloropropane and/or 2-chloropropane, and a mixture (B) which comprises epichlorohydrin, c) the mixture (A) is divided into a mixture (A1), which is returned to the first reaction stage, and a mixture (A2), d) the mixture (A2) is reacted in a second reaction stage with hydrogen peroxide in the presence of a titanium-containing zeolite catalyst in a molar ratio of allyl chloride to hydrogen peroxide in the range from 0.5:1 to 1.25:1, e) the reaction mixture formed in the second reaction stage is separated in a distillation into a mixture (C), which comprises 1-chloropropane and/or 2-chloropropane, and a mixture (D), which comprises epichlorohydrin and f) the mixture (C) is removed from the process.

In the process according to the invention, allyl chloride and hydrogen peroxide are reacted in the presence of a titanium-containing zeolite catalyst to give epichlorohydrin. The allyl chloride used here contains 1-chloropropane and/or 2-chloropropane. For the process according to the invention, it is therefore possible to use technical grades of allyl chloride which comprise 1-chloropropane and/or 2-chloropropane as by-products of the industrial preparation of allyl chloride. The content of 1-chloropropane and 2-chloropropane in the allyl chloride used is preferably in the range from 0.01 to 2% by weight, particularly preferably in the range from 0.05 to 0.8% by weight.

Hydrogen peroxide can be used as aqueous solution which preferably has a content of hydrogen peroxide in the range from 1 to 90% by weight, particularly preferably from 10 to 80% by weight and in particular from 30 to 70% by weight. Hydrogen peroxide can be used as a standard commercial stabilized solution. Likewise of suitability is nonstabilized hydrogen peroxide prepared by the anthraquinone process, which can be used without further purification, Preference is given to using a hydrogen peroxide known from WO 2004/028962 which comprises less than 50 ppm of alkali metals and alkaline earth metals, less than 50 ppm of bases with a $pK_B$ of less than 4.5 and at least 100 ppm of anions, in each case based on the weight of hydrogen peroxide.

In a further preferred embodiment, a solution of hydrogen peroxide in methanol is used which has preferably been prepared by reacting hydrogen and oxygen over a palladium catalyst in methanol. Particular preference is given to using a hydrogen peroxide solution in methanol according to Claim 9 of WO 2006/108784 which comprises 2 to 15% by weight of hydrogen peroxide, 0.5 to 20% by weight of water, 60 to 95% by weight of methanol, $10^{-6}$ to $10^{-2}$ mol/l of bromide, and also $10^{-6}$ to 0.1 mol/l of dimethyl sulphate and/or monomethyl sulphate.

Titanium-containing zeolite catalysts which can be used are any titanium-containing zeolites known from the prior art which have a catalytic activity for the reaction of olefins with hydrogen peroxide. Preferably, the titanium-containing zeolite catalyst used is a titanium silicalite with an MFI or MEL crystal structure. Particular preference is given to using titanium silicalites of the composition $(TiO_2)_x(SiO_2)_{1-x}$, where x is in the range from 0.001 to 0.05. Titanium silicalites which have been produced by the process according to WO 01/64581 or the process according to WO 01/64582 are most preferred.

The titanium-containing zeolite catalyst can be used in the process according to the invention in the form of a suspension catalyst. In this case, the reaction is preferably carried out such that the catalyst suspended in the reaction mixture is retained in the first reaction stage, for example by filtration or by sedimentation, so that the reaction mixture which is separated off in step b) in a distillation does not contain a catalyst.

Preferably, however, the titanium-containing zeolite catalyst in the process according to the invention is used in the form of a fixed-bed catalyst. Fixed-bed catalysts formed by extrusion in the form of extrudates with a diameter of from 1 to 5 mm, which preferably comprise a binder in an amount of from 1 to 99% by weight, particularly preferably 1 to 40% by weight, based on the titanium-containing zeolite, are particularly suitable. All binders which, under the reaction conditions, react neither with the hydrogen peroxide used, nor with the epichlorohydrin formed are suitable here. Particularly suitable binders are silicas. Particular preference is given to fixed-bed catalysts in which, for the extrusion, a fumed silica, a colloidal silica sol or a tetraalkyl orthosilicate or a combination of two of these components has been used as precursor for the binder. Fixed-bed catalysts which have been produced by the process known from WO 01/72419 by shaping a moulding mass which has a plateau value of the curd curve in the range from 20 to 90 mm are likewise particularly preferred.

In the process according to the invention, in step a) in the first reaction stage, allyl chloride and hydrogen peroxide are reacted in a molar ratio of allyl chloride to hydrogen peroxide of at least 1.5:1. In this case, the molar ratio of allyl chloride to hydrogen peroxide can be up to 100:1. Preferably, the molar ratio is in the range from 1.5:1 to 5:1. Particularly preferably, the molar ratio of allyl chloride to hydrogen peroxide is 2:1 to 4:1. In the case of a lower molar ratio, the selectivity for epichlorohydrin in the first reaction stage decreases. Higher molar ratios have the disadvantage that large amounts of unreacted allyl chloride have to be separated off and recycled with corresponding energy expenditure.

In step d) of the process according to the invention, in the second reaction stage allyl chloride and hydrogen peroxide are reacted in a molar ratio of allyl chloride to hydrogen peroxide in the range from 0.5:1 to 1.25:1. Preferably, the molar ratio of allyl chloride to hydrogen peroxide is 0.8:1 to 1.15:1. The use of a molar ratio in the said ranges makes it possible for allyl chloride to be converted completely or largely in the second reaction stage so that the mixture (C) obtained in step e) and removed from the process in step f) comprises only a small fraction of the allyl chloride used.

The reaction of allyl chloride and hydrogen peroxide takes place in steps a) and d) preferably in the presence of a solvent. Solvents which, under the reaction conditions, dissolve allyl chloride and hydrogen peroxide and only react with hydrogen peroxide or epichlorohydrin to a small degree, if at all, are particularly suitable. Suitable solvents are, for example, alcohols, such as methanol, ethanol or tert-butanol; glycols, such as, for example, ethylene glycol, 1,2-propanediol or 1,3-propanediol; cyclic ethers, such as, for example, tetrahydrofuran or dioxane; glycol ethers, such as, for example, ethylene glycol monomethyl ether, ethylene glycol monoethyl ether, ethylene glycol monobutyl ether or propylene glycol monomethyl ether; and also ketones, such as, for example, acetone or 2-butanone. Preferred solvents are aliphatic alcohols having 1 to 4 carbon atoms. Particular preference is given to using methanol as solvent. The fraction of solvents in the reaction mixture is, in the first reaction stage, preferably 10 to 95% by weight, particularly preferably 30 to 80% by weight, and, in the second reaction stage, is preferably 10 to 95% by weight, particularly preferably 30 to 80% by weight.

The reaction of allyl chloride and hydrogen peroxide takes place in the first reaction stage preferably at a temperature in the range from 0° C. to 100° C., particularly preferably 30° C. to 65° C. and in the second reaction stage preferably at a temperature in the range from 0° C. to 100° C., particularly preferably 30° C. to 65° C. The pressure in the reaction stages can be freely chosen within wide limits and is preferably chosen such that the boiling point of allyl chloride at the pressure used is the same as or higher than the reaction temperature used.

The reaction conditions in the first reaction stage are preferably chosen so that a conversion of hydrogen peroxide in the range from 50% to 100%, preferably from 80% to 99.8%, is achieved. In the second reaction stage, the reaction conditions are preferably chosen such that, of the components allyl chloride and hydrogen peroxide, the component used in the substoichiometric molar amount is reacted to 70% to 100%, preferably to 90% to 99%.

For the reaction of allyl chloride and hydrogen peroxide in steps a) and d) it is possible to use any reactors which are suitable for carrying out liquid-phase reactions. The reaction here can take place either batchwise or continuously, preference being given to a continuous reaction.

The reaction in steps a) and d) preferably takes place continuously in a fixed-bed reactor, where a mixture which comprises hydrogen peroxide, optionally solvent, and allyl chloride or the mixture (A2), is passed over a fixed bed of the titanium-containing zeolite catalyst. The fixed-bed reactor used is preferably an externally cooled tubular reactor, in particular a tube-bundle reactor. The fixed-bed reactor can be operated either in upward flow or in downward flow, where operation with downward flow in the trickle bed configuration is preferred.

Both in step a) and also in step d) the reaction can be carried out in two or more reactors connected in series. Preferably, in step a) two reactors connected in series are used. Both in step a) and also in step d), two or more reactors arranged in parallel can be used, such that one reactor can be taken out of operation for regenerating the catalyst and the reaction can be continued in a reactor connected in parallel.

The reaction mixture formed in the first reaction stage is separated in step b) of the process according to the invention in a distillation into a mixture (A), which comprises unreacted allyl chloride, and also 1-chloropropane and/or 2-chloropropane, and a mixture (B), which comprises epichlorohydrin. The distillation is preferably carried out as continuous rectification, where the reaction mixture formed in the first reaction stage is passed to a rectification column in a middle section, the mixture (A) is removed at the top of the column, and the mixture (B) is removed from the bottom of the column. Preference is given to using a rectification column with 10 to 50 theoretical plates. The rectification preferably takes place at a pressure at the top of the column in the range from 0.2 to 3 bar and preferably at a reflux ratio of from 0.5 to 5.

The distillation is preferably operated such that the resulting mixture (A) comprises more than 95% of the allyl chloride present in the introduced reaction mixture, and the resulting mixture (B) comprises more than 95% of the epichlorohydrin present in the introduced reaction mixture.

In step c) of the process according to the invention, the mixture (A) is divided into a mixture (A1), which is returned to the first reaction stage, and a mixture (A2), which is returned to the second reaction stage.

The mixture (A) is preferably divided such that 50% to 98%, particularly preferably 70% to 95%, of the allyl chloride present in the mixture (A) is returned with the mixture (A1) to the first reaction stage.

In a preferred embodiment, the mixture (A) is separated by a distillation so that the chloropropanes present in mixture (A) are enriched in the mixture (A2).

In step e) of the process according to the invention, the reaction mixture formed in the second reaction stage is separated in a distillation into a mixture (C), which comprises 1-chloropropane and/or 2-chloropropane, and a mixture (D), which comprises epichlorohydrin. The distillation is preferably carried out as continuous rectification, where the reaction mixture formed in the second reaction stage is passed to a rectification column in a middle section, the mixture (C) is removed at the top of the column, and the mixture (D) is removed from the bottom of the column. Preferably, a rectification column with 10 to 50 theoretical plates is used. The rectification preferably takes place at a pressure at the top of the column in the range from 0.5 to 3 bar and preferably at a reflux ratio of from 0.5 to 5.

The distillation is preferably operated such that the resulting mixture (C) comprises more than 90% of the chloropropanes present in the introduced reaction mixture, and the resulting mixture (D) comprises more than 95% of the epichlorohydrin present in the introduced reaction mixture.

In a preferred embodiment, the mixture (D) obtained in step e) of the process according to the invention is returned to the first reaction stage. This embodiment is particularly advantageous if, in step d), hydrogen peroxide is used in molar excess and the mixture (D) still comprises unreacted hydrogen peroxide. As a result of the recycling to the first reaction stage, this unreacted hydrogen peroxide can still be utilized for the epoxidation of further allyl chloride. In a particularly preferred embodiment, the first reaction stage is carried out in two reactors connected in series and the mixture (D) is returned to the second reactor.

In a further embodiment, steps d) and e) of the process according to the invention take place simultaneously in the form of a reactive distillation. In this embodiment, the titanium-containing zeolite catalyst of the second reaction stage is arranged in a reaction section of a rectification column, the mixture (A2) is introduced into the column at a point below the reaction section, and the hydrogen peroxide is introduced at a point above the reaction section. The mixture (C) is removed at the top of the column, and the mixture (D) is removed from the bottom of the column.

FIG. 1 shows diagrammatically a preferred embodiment of the claimed process in which the reactions in steps a) and d) take place in fixed-bed reactors and the distillations in steps b) and e) are carried out in distillation columns. The auxiliary units required for carrying out the process, such as pumps, heat exchangers, evaporators and condensers, are not shown. In the process of FIG. 1, in steps a) and e), nitrogen is additionally fed in as inert gas in order to prevent a formation of combustible gas mixtures. Hydrogen peroxide (1), allyl chloride (2), methanol (3) and nitrogen (4) are introduced into the first fixed-bed reactor (a). The reaction mixture obtained in the first fixed-bed reactor (a) is separated in the distillation column (b) into a top product (7), which comprises allyl chloride and unreacted chloropropanes (mixture A), a bottom product (5), which comprises epichlorohydrin (mixture B), and also a waste gas stream (6). The mixture A is then divided in (c) into a stream (8) which is returned to the first fixed-bed reactor (a) (mixture A1) and a stream (9) which is fed to the second fixed-bed reactor (d) (mixture A2) where it is reacted with further hydrogen peroxide (10). The reaction mixture obtained in the second fixed-bed reactor (d) is separated in the distillation column (e) into a top product (12), which comprises the chloropropanes (mixture C), and a bottom product (13), which comprises epichlorohydrin (mixture D) and is returned to the first fixed-bed reactor (a). Nitrogen (11) is additionally fed to the distillation column (e).

EXAMPLES

Example 1

Influence of the Molar Ratio of Allyl Chloride to Hydrogen Peroxide on the Selectivity of the Reaction Allyl chloride was reacted with hydrogen peroxide in methanol as solvent using a titanium silicalite catalyst with MFI structure. The reaction was carried out in two tubular reactors connected in series which were cooled via a cooling mantle. The catalyst was used as fixed bed in the form of extrudates. The first reactor contained 21.5 g of catalyst, the second reactor 20.7 g. Allyl chloride and a mixture of an aqueous hydrogen peroxide solution and methanol were continuously introduced into the first reactor. The metered quantitative streams, the composition of the mixture and the molar ratio of allyl chloride to hydrogen peroxide in the starting materials are given in Table 1. The reactors were operated in upward flow operation, the pressure in the reactors being kept at 7 to 8 bar and the first reactor being heated to 36° C. and the second reactor being heated to 38° C. In the reaction mixture obtained, the content of hydrogen peroxide was determined by redox titration and the contents of allyl chloride and epichlorohydrin were determined by gas chromatography. The conversions of hydrogen peroxide and selectivities for epichlorohydrin calculated from these contents and based on reacted allyl chloride are given in Table 1. Table 1 shows that the selectivity for epichlorohydrin increases with increasing molar excess of allyl chloride.

TABLE 1

| Composition of the $H_2O_2$/MeOH mixture in % by wt. | | | Metered quantitative streams in g/h | | Allyl | $H_2O_2$ | Selectivity for |
| --- | --- | --- | --- | --- | --- | --- | --- |
| $H_2O_2$ | Water | MeOH | $H_2O_2$/MeOH mixture | Allyl chloride | chloride/$H_2O_2$ molar ratio | conversion in % | epichloro- hydrin in % |
| 10.5 | 7.9 | 81.1 | 73.1 | 28.7 | 1.7 | 84.5 | 88.3 |
| 8.4 | 6.3 | 85.3 | 72.8 | 29.0 | 2.1 | 85.1 | 88.8 |

TABLE 1-continued

| Composition of the $H_2O_2$/MeOH mixture in % by wt. | | | Metered quantitative streams in g/h | | Allyl chloride/$H_2O_2$ molar ratio | $H_2O_2$ conversion in % | Selectivity for epichloro-hydrin in % |
|---|---|---|---|---|---|---|---|
| $H_2O_2$ | Water | MeOH | $H_2O_2$/MeOH mixture | Allyl chloride | | | |
| 8.4 | 6.3 | 85.3 | 73.2 | 43.3 | 3.1 | 85.8 | 91.0 |
| 10.5 | 7.9 | 81.1 | 72.0 | 57.9 | 3.4 | 87.6 | 92.6 |
| 10.5 | 7.9 | 81.1 | 64.4 | 58.3 | 3.8 | 88.5 | 92.9 |
| 8.4 | 6.5 | 85.0 | 73.0 | 58.1 | 4.2 | 90.3 | 93.2 |
| 8.0 | 5.9 | 86.2 | 72.7 | 71.8 | 5.5 | 88.0 | 94.4 |

Example 2

Process According to FIG. 1

For the process of FIG. 1, the reactions in the fixed-bed reactors (a) and (d) were experimentally reproduced in a tubular reactor corresponding to Example 1 for a molar ratio of allyl chloride to hydrogen peroxide of 4.0 in reactor (a) and 1.1 in reactor (b). For this purpose, the reactor contained 42.6 g of catalyst and was heated to 40° C. The metered quantitative streams, the composition of the mixture of hydrogen peroxide, water and methanol and the molar ratio of allyl chloride to hydrogen peroxide in the starting materials are given in Table 2, the values chosen being those which arise on the basis of the returns in the process of FIG. 1. Then, using the experimentally determined selectivities and an estimation of the reactivity of 1-chloropropene relative to allyl chloride, the composition of the quantitative streams 1 to 13 was calculated for the process of FIG. 1 using the simulation program Aspen Plus from Aspentech. The results are given in Table 3.

In the process of FIG. 1, 1.12 mol of allyl chloride are required for the preparation of one mole of epichlorohydrin. By contrast, in a process corresponding to the prior art, in which the amount of allyl chloride present in stream 9 is eliminated from the process, 1.35 mol of allyl chloride are required for the preparation of one mole of epichlorohydrin.

TABLE 2

| Composition of the $H_2O_2$/MeOH mixture in % by wt. | | | Metered quantitative streams in g/h | | Allyl chloride/$H_2O_2$ molar ratio | Selectivity for epichloro-hydrin in % |
|---|---|---|---|---|---|---|
| $H_2O_2$ | Water | MeOH | $H_2O_2$/MeOH mixture | Allyl chloride | | |
| 7.7 | 7.9 | 84.4 | 80.2 | 58.2 | 4.0 | 92.9 |
| 8.7 | 6.2 | 85.1 | 106.6 | 23.7 | 1.1 | 87.9 |

TABLE 3

| Component | Material stream and fraction of the component in the material stream in g/h | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 12 |
| $N_2$ | 0.0 | 0.0 | 0.0 | 10.0 | 0.0 | 10.0 | 0.0 | 0.0 | 0.0 | 0.0 | 3.8 | 2.5 | 0.0 |
| $O_2$ | 0.0 | 0.0 | 0.0 | 0.0 | 0.0 | 1.7 | 0.0 | 0.0 | 0.0 | 0.0 | 0.4 | 0.0 | 0.0 |
| 2-Chloropropane | 0.0 | 1.0 | 0.0 | 0.0 | 0.0 | 0.0 | 9.9 | 8.9 | 1.0 | 0.0 | 0.0 | 1.0 | 0.0 |
| 1-Chloropropene | 0.0 | 0.7 | 0.0 | 0.0 | 0.0 | 0.0 | 6.4 | 5.9 | 0.5 | 0.0 | 0.0 | 0.5 | 0.0 |
| Allyl chloride | 0.0 | 464.9 | 0.0 | 0.0 | 0.0 | 0.0 | 1190.1 | 1101.0 | 89.1 | 0.0 | 0.0 | 8.9 | 0.0 |
| 1-Chloropropane | 0.0 | 1.1 | 0.0 | 0.0 | 0.0 | 0.0 | 14.7 | 13.6 | 1.1 | 0.0 | 0.0 | 1.1 | 0.0 |
| MeOH | 0.0 | 0.0 | 17.2 | 0.0 | 0.4 | 0.0 | 771.7 | 713.9 | 57.7 | 0.0 | 0.0 | 0.9 | 52.8 |
| Water | 75.0 | 0.0 | 0.0 | 0.0 | 201.0 | 0.0 | 4.9 | 4.5 | 0.4 | 15.5 | 0.0 | 0.0 | 35.0 |
| Epichlorohydrin | 0.0 | 0.0 | 0.0 | 0.0 | 500.4 | 0.0 | 17.0 | 15.7 | 1.3 | 0.0 | 0.0 | 0.0 | 84.3 |
| $H_2O_2$ | 175.0 | 0.0 | 0.0 | 0.0 | 0.0 | 0.0 | 0.0 | 0.0 | 0.0 | 36.2 | 0.0 | 0.0 | 0.0 |
| 3-Chloro-1-methoxy-2-propanol | 0.0 | 0.0 | 0.0 | 0.0 | 64.5 | 0.0 | 0.0 | 0.0 | 0.0 | 0.0 | 0.0 | 0.0 | 17.7 |

We claim:
1. A process for the preparation of epichlorohydrin comprising:
 a) reacting, in a first reaction stage, impure allyl chloride and hydrogen peroxide in the presence of a titanium-containing zeolite catalyst in a molar ratio of allyl chloride to hydrogen peroxide of at least 1.5:1 and where the impure allyl chloride has impurities of 1-chloropropane and/or 2-chloropropane,
 b) separating the reaction mixture formed in the first reaction stage into a mixture (A) which comprises unreacted allyl chloride, and 1-chloropropane and/or 2-chloropropane, and a mixture (B) which comprises epichlorohydrin,
 c) dividing the mixture (A) into a mixture (A1), which is returned to the first reaction stage, and a mixture (A2), d) reacting, in a second reaction stage, the mixture (A2) with hydrogen peroxide in the presence of a titanium-containing zeolite catalyst in a molar ratio of allyl chloride to hydrogen peroxide in the range from 0.5:1 to 1.25:1, e) separating the reaction mixture formed in the second reaction stage into a mixture (C), which comprises 1-chloropropane and/or 2-chloropropane, and a mixture (D), which comprises epichlorohydrin and f) removing the mixture (C) from the process.

2. The process of claim 1, wherein steps a) and d) take place in the presence of a solvent.

3. The process of claim 2, wherein the solvent is methanol.

4. The process of claim 3, wherein the hydrogen peroxide is in the form of a solution of hydrogen peroxide in methanol.

5. The process of claim 1, wherein in step a) the molar ratio of allyl chloride to hydrogen peroxide is in the range from 1.5:1 to 5:1.

6. The process of claim 1, wherein the dividing of the mixture (A) in step c) takes place by a distillation in which the 1-chloropropane and/or 2-chloropropane present in mixture (A) are enriched in the mixture (A2).

7. The process of claim 1, wherein the mixture (D) is returned to the first reaction stage.

8. The process of claim 1, wherein the first reaction stage is carried out in two reactors connected in series and the mixture (D) is returned to the second reactor.

9. The process of claim 1, wherein steps d) and e) take place simultaneously in a reactive distillation.

\* \* \* \* \*